United States Patent [19]

Mehta

[11] 4,326,404
[45] Apr. 27, 1982

[54] RESPIRATORY MONITOR

[76] Inventor: Jasu G. Mehta, 15 Stonewall La., Mamaroneck, N.Y. 10543

[21] Appl. No.: 126,667

[22] Filed: Mar. 3, 1980

[51] Int. Cl.³ ............................................. A61B 5/08
[52] U.S. Cl. ...................................... 73/29; 128/721; 128/724
[58] Field of Search ...................... 128/719, 721, 724; 73/1 G, 29, 73; 252/521; 324/65 R, 65 CR, 65 CP, 65 P; 338/34–35

[56] References Cited

U.S. PATENT DOCUMENTS 2,064,651 12/1936 Fiene ...................................... 338/35
3,831,707 8/1974 Takeuchi .......................... 128/719 X
3,935,742 2/1976 Rybak ................................ 338/35 X Primary Examiner—Robert W. Michell
Assistant Examiner—Francis J. Jaworski
Attorney, Agent, or Firm—Darby & Darby

[57] ABSTRACT

An apparatus for detecting the quantity of moisture in a given region includes a crystal of sodium chloride, a support for the crystal in the region and means for detecting the change in the electrical resistance of the crystal caused by the exposure of the crystal to moisture. A dry gas is caused to flow intermittently over the crystal to remove the accumulated moisture from it. This prevents the crystal from dissolving and allows the use of a smaller crystal than would otherwise be possible.

11 Claims, 4 Drawing Figures

RESPIRATORY MONITOR

BACKGROUND OF THE INVENTION

This invention relates generally to humidity detectors and, more particularly, to a humidity detector utilizing a sensing element comprising a single crystal of sodium chloride which is particularly adapted for use as a respiratory monitor.

A device which is capable of providing an indication of the respiratory rate of a patient and/or providing an audible or visual alarm upon the cessation of respiration is useful in a number of clinical situations. For example, such a device may be advantageously employed during operative procedures and for monitoring patients in the post-operative and intensive care units of a hospital. Various types of respiratory monitors have been employed in such situations.

One such monitor, for example, is sensitive to the movements of the patient's chest associated with breathing. A disadvantage of this type of monitor is that, where the patient's trachea is partially or completely blocked, his chest may continue to move in accordance with his attempts to breath. Under such conditions a respiratory monitor which is reponsive only to chest movement may falsely indicate normal breathing where in fact the patient's attempts to breath are actually ineffective.

Other known respiratory monitors utilize a thermistor as a sensing element. The thermistor may, for example, be installed in a tube which is adapted for insertion into the trachea of the patient. Typically, the thermistor is connected to an electrical circuit which heats the thermistor to a predetermined temperature at which its electrical resistance is known. As air passes by the thermistor due to inhalations or exhalations of the patient, the thermistor is cooled causing corresponding increases in its resistance. These changes in the resistance of the thermistor may be detected by known means to determine the rate of respiration of the patient.

Since the thermistor as a sensing element has to be heated, it cannot be introduced in the nose or the trachea and it cannot be used in the presence of anesthetics in the operating room.

U.S. Pat. No. 3,935,742 to Rybak describes a respiratory monitor utilizing a sensing element which is responsive to changes in the moisture content of the air to which it is exposed. This sensing element uses a thread formed of a rubber or plastic material having a high electrical resistance. The element is installed across the opening of a mouthpiece and is connected to a voltage source. When the patient exhales, moisture condenses on the surface of the thread; the subsequent evaporation of the moisture during inhalation lowers the electrical resistance of the element. These changes in resistance and the corresponding changes in the amount of current flowing through the element may be detected by conventional means to give an indication of respiration.

The apparatus described by Rybak suffers from a number of disadvantages. First, the film of moisture deposited on the sensing element during exhalation may not completely evaporate during inhalation. Rybak suggests that evaporation of the condensation water layer may be accelerated by heating the sensing element. However, such heating may prove dangerous in environments in which explosive gases are present.

Second, since the sensing element of Rybak is exposed to the ambient air surrounding the patient, the accuracy of the measurements obtained may be adversely affected by variations in the relative humidity of the ambient atmosphere.

Also, the relatively long sensing element required in the Rybak apparatus is suitable for installation only across a similarly large opening, such as may be provided in a mouthpiece. A narrow tube, such as a prong of a nasal cannula for supplying oxygen to the nostril of a patient, does not provide an opening large enough to accommodate the moisture-sensitive element suggested by Rybak. Moreover, under certain circumstances, it may be undesirable to insert the mouthpiece required by Rybak into a patient's mouth.

The use of a salt in a moisture sensitive element is known in the art. For example, U.S. Pat. No. 2,975,638 of Morrison discloses a moisture sensitive element in which a salt film is connected in parallel with a thermocouple. Current is passed through the film to heat it and drive off condensed moisture. The thermocouple, on the other hand, tends to extract heat from the film and an equilibrium balance is reached at which the film contains an equilibrium water content. The heating of the salt film required by the Morrison patent is believed to render this type of moisture sensitive element unsuitable for use in the presence of explosive gasses.

U.S. Pat. No. 2,064,651 of Fiene sets forth the use of a solid block of fused salt other than sodium chloride as a moisture sensitive element. The element of Fiene does not offer the advantage of the relatively small size of the single crystal of sodium chloride which is utilized as the sensing element of the present invention.

In accordance with the present invention, therefore, a respiratory monitor is disclosed which overcomes the disadvantages discussed above and offers a number of other important advantages.

GENERAL DESCRIPTION OF THE INVENTION

In accordance with the present invention, a respiratory monitor is provided which utilizes as a sensing element a transducer comprising a single crystal of sodium chloride of relatively small dimensions (e.g., 2 mm×2 mm×10 mm). Such a crystal has the property of lowering its resistance upon exposure to moisture. Because of its relatively small dimensions, it may be installed within a tube of relatively small cross-sectional area, such as a catheter or one of the prongs of a nasal cannula of the type utilized to supply oxygen to a patient.

In a preferred embodiment of the invention, therefore, the sodium chloride transducer is installed within such a tube, adjacent the end of the tube which is to be inserted into the patient's nostril or trachea. Two electrical leads are connected to the transducer to connect it to appropriate excitation and sensing circuitry. In its simplest form, this circuitry may be adapted merely to actuate an audio indicator (e.g., a buzzer) or some visual indicator upon a lowering of the resistance of the sodium chloride transducer. This would be indicative of exposure of the transducer to the moisture contained in the breath exhaled by the patient. The repetition of such indications yields the patient's rate of breathing. Alternatively, the circuitry may include a counter which counts the number of exhalations in a given period of time.

An important feature of the invention is a provision for introducing a monitored flow of dry gas (e.g., oxygen) into the end of the tube opposite the end at which the transducer is installed. The rate of flow of dry gas into the tube is adjusted so that when the patient is not exhaling the dry gas will pass over the transducer and will remove any accumulated moisture from it. The rate of flow of dry gas is maintained at a low enough level, however, so that when the patient exhales the exhaled moisture-laden air is caused to pass over the transducer to lower its resistance for the duration of the exhalation. Use of this dry gas increases the reliability of the transducer, simplifies the associated circuitry and prolongs the life of the transducer by slowing its rate of dissolution.

Another embodiment of the invention provides a quantitative measure of moisture content in a given area such as the tracheo-bronchial tree of an animal or human. In accordance with this embodiment a sodium chloride transducer of the type just described is incorporated as one leg of a bridge network. A second leg of the bridge network includes a reference transducer which is a sodium chloride crystal having essentially identical properties to the moisture-sensing transducer. The bridge is initially balanced with both crystals maintained in a dry state by passing dry gas such as oxygen over them. Subsequently, the reference crystal is continued to be maintained in its dry state by providing it with a continuing supply of dry gas while the moisture-sensing transducer, which may be installed at the tip of a catheter, is inserted, for example, into the trachea. Since the resistance of the moisture-sensing transducer is reduced in relation to the amount of moisture to which it is exposed, and the resistance of the reference crystal remains unchanged, the bridge becomes unbalanced and a voltage appears at its output terminals. This voltage is related to the quantity of moisture to which the moisture-sensing transducer is exposed. A quantitative measurement of moisture content can be obtained in this way.

It is an object of the present invention, therefore, to provide a respiratory monitoring apparatus which provides accurate measurements of respiration and its rate regardless of variations in the temperature, pressure or composition of the gases exhaled by a patient.

It is a further object of the present invention to avoid affecting the accuracy of measurement of the respiratory monitor by variations in the relative humidity of the ambient air.

It is a further object of the invention to cause the apparatus to be resistant to physical shocks or vibrations.

It is a still further object of the invention to make the apparatus safe for use in the presence of explosive gases, such as anesthetic gases.

It is yet a further object of the invention to provide an apparatus having a sensor which may remain in place during defibrillation of and other procedures on the patient.

It is a still further object of the invention to provide apparatus yielding accurate quantitative measurements of moisture content in interior areas (such as the tracheobronchial tree) of a person or animal.

DETAILED DESCRIPTION

The scope of this invention is defined with particularity in the appended claims. An understanding of the above and further objects of this invention may be obtained by referring to the following description of a preferred embodiment, in conjunction with the appended drawings, in which:

Figure 3:
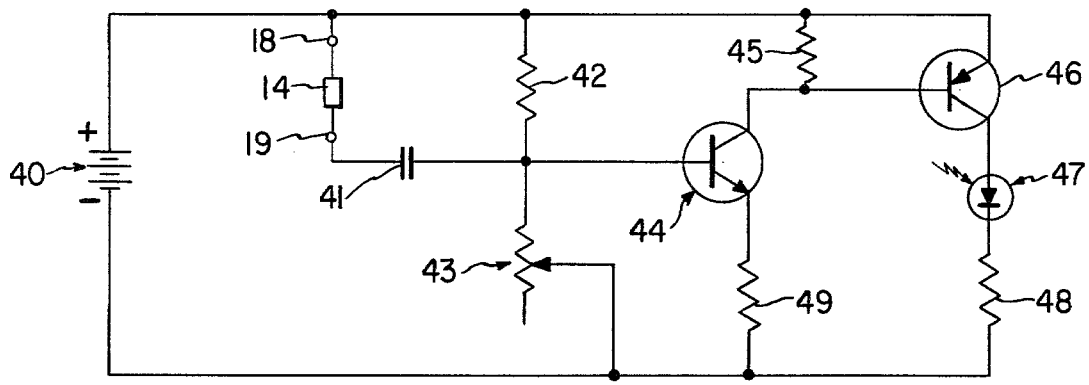
Figure 4:
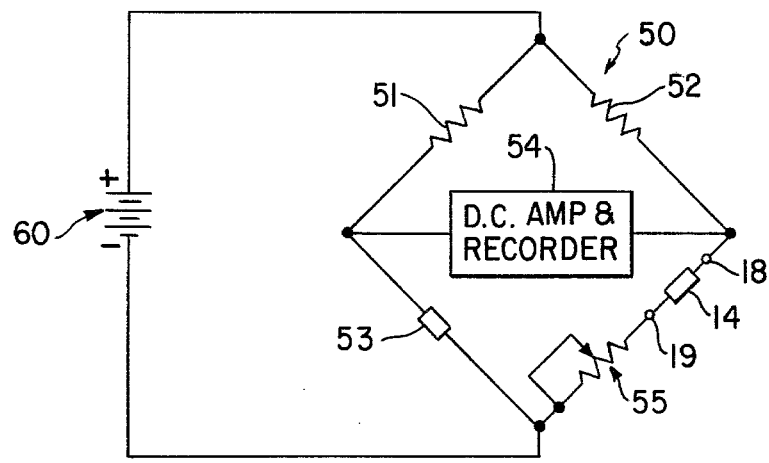

FIG. 3 is a circuit diagram of an embodiment of the invention employing the sodium chloride transducer to activate a visual indicator during the period in which a patient is exhaling; and FIG. 4 is a circuit diagram of an embodiment of the invention employing the sodium chloride transducer for obtaining a quantitative indication of the quantity of moisture in the atmosphere in a given region, such as the interior of the trachea.

Figure 1:
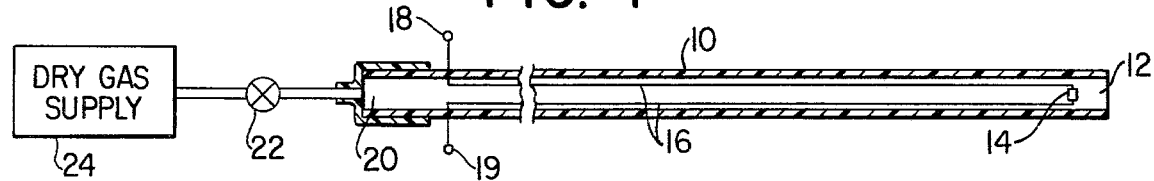
FIG. 1 is a diagrammatic view showing the typical placement of the sodium chloride transducer of the present invention in a narrow plastic tube.

FIG. 1 illustrates the manner in which a moisture-sensitive transducer 14 comprising a sodium chloride crystal is installed within a plastic tube 10 in accordance with the present invention in order to perform the desired function of monitoring the rate of a patient's respiration by sensing the relatively high moisture content of the patient's exhaled breath.

A crystal which is suitable for use as the transducer 14 of the present invention is a single crystal of relatively pure sodium chloride having dimensions in the order of 2 mm $\times$ 2 mm $\times$ 10 mm. Such crystals are presently used as filters for lasers and in infrared analyzers, and are commercially available from companies such as International Crystal Laboratories.

The ends of transducer 14 are connected respectively to a pair of electrical leads 16, by any suitable means, such as a conductive cement. The transducer 14 is positioned near one opening 12 of a plastic tube 10 which preferably has a diameter in the order of $\frac{1}{4}$ of an inch or less. Such a tube may, for example, comprise a catheter which is adapted for insertion into a patient's trachea, or it may be one of the prongs of a nasal cannula of the type utilized to supply oxygen to the nostrils of a patient. The transducer 14 is preferably positioned in the tube 10 closely adjacent to the opening 12 of the tube into which the patient will exhale. The electrical leads 16 are passed through the interior of the tube 10 and are brought out to a pair of respective terminals 18 and 19. As illustrated by FIG. 1, the terminals 18 and 19 are positioned at points on the sides of the tube 10. It will be understood, however, that terminals 18 and 19 may be located at any convenient position. For example, the electrical leads 16 may pass through the opening 20 of the tube 10 which is opposite its opening 12 and the terminals 18 and 19 may be located at any position which is convenient to the opening 20 of the tube.

A particularly advantageous feature of the present invention is its means for drying the transducer 14 during the periods between exhalations. This means includes a supply of dry gas 24 (e.g., oxygen) which is connected to the opening 20 of the tube 10 through a valve 22. The flow of dry gas through the tube 10 may be adjusted by means of the valve 22 so that during the periods between exhalations a flow of dry gas is maintained past the transducer 14, but when the patient exhales the moist exhaled air is allowed to flow past the transducer 14 in the direction opposite the flow of dry gas.

Figure 2:
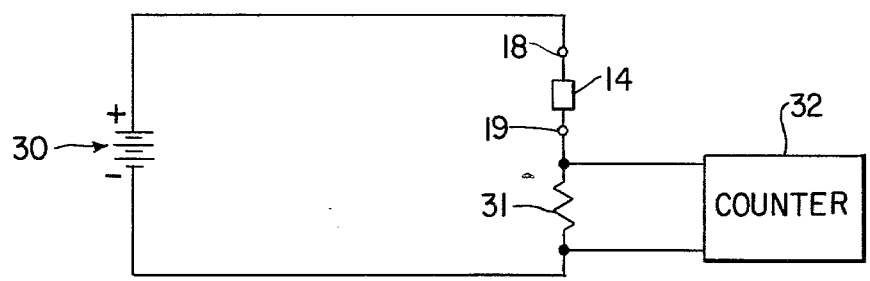
FIG. 2 is a circuit diagram of an embodiment of the invention employing the sodium chloride transducer to drive a respiration counter.

FIG. 2 illustrates a circuit employing the apparatus illustrated by FIG. 1 to drive a counting apparatus for determining the respiration rate of the patient. As illustrated by FIG. 1, the sodium chloride transducer 14 is connected via the terminal 18 to a voltage source 30 such as a conventional 9 volt battery. The other side of the transducer 14 is connected via the terminal 19 to a resistor 31 which in turn is connected to the other side of the voltage source 30. A conventional respiratory counting apparatus 32 (such as a Hewlett-Packard model 78202B counter) is connected across the resistor 31.

The operation of the circuit of FIG. 2 is as follows. Each time the patient exhales, the transducer 14 is exposed to the relatively high moisture content of the exhaled air. During the exhalation, therefore, the resistance of the transducer 14 becomes lower, and allows a larger current to flow through the resistor 31. The voltage drop across the resistor 31 thus reaches a peak during each exhalation period. During the periods between exhalations, the dry gas passing over the transducer 14 removes the accumulated moisture from the transducer, which allows it to return to its original resistance value. The counting apparatus 32 senses the voltage signal across the resistor 31 and increments a counter in response to each of the voltage peaks produced across the resistor 31. The counting apparatus 32 may include features such as a digital readout for indicating the number of exhalations per minute of the patient. The counting apparatus 32 may also include means for preselecting maximum and minimum allowable values of respiration rate, and means for comparing the detected respiration rate with these predetermined values for activating an appropriate alarm upon an excursion of the detected respiration rate beyond the predetermined limits.

FIG. 3 illustrates an embodiment of the invention in which each exhalation is indicated by the activation of a visual indicator. This embodiment of the invention would be particularly useful for monitoring respiration in darkened areas, such as X-ray rooms or cardiac labs.

As indicated by FIG. 3 a sodium chloride transducer 14, which appropriately mounted as described above, is connected to the positive terminal of a voltage source 40. Also connected to the positive terminal of the voltage source 40 is a resistor 42, a resistor 45, and the emitter of a PNP transistor 46. The transducer 14 is connected in series with a capacitor 41, and the resistor 42 is connected across the series combination of the transducer 14 and the capacitor 41. The base of an NPN transistor 44 is connected to the point of interconnection of the resistor 42 and the capacitor 41 and is also connected back to the negative terminal of the voltage source 40 through a variable resistor 43. The resistance value of the resistor 42 and the range of resistance values of the variable resistor 43 are selected to provide an excitation voltage across the transducer 14 which ranges between zero volts and approximately 50 millivolts. Under these conditions the flow of current through the transducer 14 will range between approximately 0 and 6 microamperes.

The collector of the transistor 44 is connected to the base of the transistor 46 and is also connected to the positive terminal of the voltage source 40 through the resistor 45. The emitter of the transistor 44 is connected to the negative terminal of the voltage source 40 through a resistor 49. The collector of the transistor 46 is connected to the negative terminal of the voltage source 40 through a series circuit comprising a light emitting diode (LED) 47 and a resistor 82.

Prior to utilizing the apparatus illustrated by FIG. 3 for monitoring the respiration of a patient it should be calibrated as follows. The bias voltage applied to the base of the transistor 44 is appropriately set by adjusting the variable resistor 43 until the light emitting diode 47 ignites; then the variable resistor 43 is readjusted to the point at which the LED 47 just goes off. The valve 22 of FIG. 1 is then adjusted so that the LED 47 ignites during exhalations and turns off during inspiration (inhalation).

The operation of the circuit of FIG. 3 is as follows. During the calibration procedure the resistance value of the variable resistor 43 is set to a value at which the voltage at the base of the transistor 44 will be low enough to prevent the transistor 44 from conducting when the transducer 14 is dry and has a relatively high resistance value. The exposure of the transducer 14 to the moisture of a patient's exhaled breath causes the resistance of the transducer 14 to become lower. This decrease in the resistance of transducer 14 allows an increased current to flow through the resistor 43 which causes the voltage at the base of the transistor 44 to increase to the point at which transistor 44 becomes conductive. The resulting flow of current through the resistor 45 results in a decrease in the voltage applied to the base of the PNP transistor 46 which causes transistor 46 to become conductive. The flow of current through the transistor 46 passes through the light emitting diode 47 and the resistor 48 to cause the light emitting diode 47 to ignite.

The apparatus described above incorporates a number of useful features. For example, the apparatus indicates regular breathing of the patient by a corresponding regular flashing of the light-emitting diode 47. This feature is particularly useful in situations where the patient is in a darkened room such as an x-ray room. The light-emitting diode may, of course, be replaced by any other convenient visual indicator or by an audible indicator such as a buzzer, to obtain the same or similar effect. Since the LED remains on as long as an exhalation continues, the duration and pattern of exhalations are visually indicated. The duration of each exhalation corresponds roughly to the volume of air exhaled.

A further advantage of this apparatus is that, if the patient's air passage becomes obstructed, and prevents him from ventilating, the indicator light will remain off, which indicates this dangerous condition. Under these circumstances the patient's chest walls may continue to move so that a respiratory monitor which is responsive to chest movement of the patient would be incapable of detecting such a dangerous condition.

Still another advantage of the apparatus just described is the relatively low excitation voltage (in the order of 0 to 50 millivolts at 0 to 6 microamps) needed to drive the transducer 14, and the lack of any need to heat the transducer to remove accumulated moisture from it. Because of these features the apparatus is safe for use in essentially any environment, including environments such as an operating room, in which the transducer 14 may be exposed to explosive gases. Since the transducer can be installed in the nostril, it is of particular use in monitoring respirations during certain ENT, EYE and NECK operations which are performed under heavy sedation and where the patient is draped so that the direct observation of the patient is not possible.

FIG. 4 illustrates an embodiment of the invention which is particularly adapted to provide a quantitative measurement of the humidity in a region, such as the tracheo-bronchial tree of animals or persons. A bridge circuit 50 is connected across the terminals of a power source 60. Two legs of the bridge 50 are formed by respective resistors 51 and 52 which have essentially identical resistance values.

A third leg of the bridge comprises the series combination of a sodium chloride transducer 14 as described above and a potentiometer 55. The last leg of the bridge is formed by a sodium chloride reference crystal 53 having electrical and physical characteristics essentially identical to those of the sodium chloride transducer 14. The output terminals of the bridge 50 may be connected to any convenient measurement apparatus, such as the d.c. amplifier and recorder 54 illustrated by FIG. 4.

Prior to performing measurements, a dry gas is caused to flow over the reference crystal 53 and the transducer 14. The potentiometer 55 is then adjusted to obtain a zero reading from the measurement apparatus 54. After the bridge 50 is thus balanced, the supply of dry gas to the transducer 14 is turned off but the supply of dry gas to the reference crystal 53 is maintained. The transducer 14, which, as illustrated by FIG. 1, may be installed within the end of a catheter, is then inserted into the area of investigation. For example, the catheter may be lowered into the trachea of a patient. The lowering of the resistance of the transducer 14 caused by its exposure to the moisture in the trachea unbalances the bridge, causing a voltage to appear across the terminals of the measuring apparatus 54. The magnitude of this voltage is functionally related to the amount of moisture to which the transducer 14 is exposed. The magnitude of this voltage thus provides a quantitative indication of the quantity of moisture in the area under investigation.

It will be understood that the foregoing description of a number of illustrative embodiments of the present invention is for the purposes of illustration only, and that various structural and operational features of the invention may be modified without departing from the spirit and scope of the present invention as defined in the appended claims.

What is claimed is:

1. Apparatus for detecting the quantity of moisture in a gas in a given region comprising:
    a crystal of sodium chloride;
    a support for said crystal in said region;
    means operatively connected to said crystal for detecting a change in the electrical resistance of said crystal caused by exposure of said crystal to moisture; and
    means for intermittently supplying a flow of dry gas over said crystal sufficient to remove accumulated moisture therefrom.

2. Apparatus in accordance with claim 1 wherein said support comprises a tube, said crystal being mounted within said tube adjacent an opening thereof.

3. Apparatus in accordance with claim 2 wherein said tube has a diameter less than approximately one quarter of an inch.

4. Apparatus in accordance with claim 2 for monitoring the rate of respiration of a patient, wherein said tube is adapted for placing said crystal in close proximity to a respiratory passage of said patient and wherein said gas supply means comprises:
    means connected to a second opening of said tube for supplying a flow of said dry gas over said crystal sufficient to remove accumulated moisture from said crystal during periods in which the patient is not exhaling, said flow being insufficient to prevent exhaled air from entering said opening and flowing over said crystal during periods of exhalation.

5. Apparatus in accordance with claim 4 wherein said detecting means comprises:
    an impedance of predetermined value connected in series circuit relationship with said crystal;
    a source of electrical voltage connected across said series circuit; and
    a counter circuit operatively connected to said impedance for counting the number of variations in the magnitude of the current flowing through said impedance resulting from corresponding variations in the impedance of said crystal caused by exposure of said crystal to said exhaled air.

6. Apparatus in accordance with claim 4 wherein said detecting means comprises:
    an indicating device;
    a circuit operatively connected to said crystal and to said indicating device and responsive to a variation in the impedance of said crystal from a predetermined value for activating said indicating device.

7. Apparatus in accordance with claim 6 wherein said activating means is adapted to activate said indicating device for a period of time corresponding to the duration of said impedance variation.

8. Apparatus in accordance with claim 1 wherein said detecting means comprises:
    a reference device having electrical characteristics essentially identical to those of said crystal; and
    means operatively connected to said reference device and said crystal for generating a signal having a magnitude related to the difference between the resistance of said reference device and said crystal.

9. Apparatus in accordance with claim 8 wherein said reference device comprises:
    a second crystal of sodium chloride having electrical characteristics which are essentially identical to the electrical characteristics of said first crystal; and
    means for maintaining said second crystal in a dry state.

10. Apparatus in accordance with claim 9 wherein said maintaining means comprises:
    a supply of dry gas adapted to flow over said second crystal.

11. Apparatus in accordance with claim 8 wherein said signal-generating means comprises:
    a bridge circuit having a first leg including said reference means and a second leg including said crystal.

* * * * *